US00PP11905P2

(12) United States Plant Patent
Glicenstein

(10) Patent No.: US PP11,905 P2
(45) Date of Patent: Jun. 5, 2001

(54) CHRYSANTHEMUM PLANT NAMED 'SOFT HEATHER'

(75) Inventor: Leon Glicenstein, State College, PA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/224,730

(22) Filed: Jan. 4, 1999

(51) Int. Cl.[7] ..... A01H 5/00
(52) U.S. Cl. ..... Plt./287
(58) Field of Search ..... Plt./287, 291, 292

(56) References Cited

U.S. PATENT DOCUMENTS

P.P. 9,440 * 1/1996 VandenBerg ..... Plt./287
4,616,099 * 10/1986 Sparkes ..... 47/58

OTHER PUBLICATIONS

Broertjes, et al., 1980, "A mutant of a mutant of a . . . Irradiation of progressive radiation–induced mutants in a mutation breeding programme with *Chrysanthemum morifolium*", Euphytica, 29: 525–530.*

Gosling, ed., 1979, "The Chysanthemum Manual—6$^{th}$ edition", The National Chrysanthemum Society, London, Essex Telegraph Press, Ltd., pp. 329–336.*

Broertjes, 1978, "Application of Mutation Breeding Methods in the Improvement of Vegetatively Propagated Crops", Elsevier Sci. Pub. Co., New York, pp. 162–175.*

Searle, et al., 1968, "Chrysanthemums The Year Round", Blanford Press, London, pp. 27–29, 320–327.*

Chan, 1966, "Chrysanthemum and rose mutations induced by X–rays", Am. Soc. Hort. Sci. Proc., pp. 613–620.*

Broertjes, 1966, "Mutation breeding of chrysanthemums", Euphytica, 15: 156–162.*

Dowrick, et al., 1966, "The induction of mutations in chrysanthemum using x– and gamma radiation", Euphytica, 15: 204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Soft Heather', characterized by its uniformly mounded plant habit; decorative-type inflorescences that are about 4.5 cm in diameter; attractive lavender-colored ray florets; numerous inflorescences per plant; and very uniform flowering.

1 Drawing Sheet

BACKGROUND OF THE INVENTION

The present invention relates to a new and distinct cultivar of Chrysanthemum plant, botanically known as *Dendranthema grandiflora* and referred to by the cultivar name Soft Heather.

The new cultivar is a product of a mutation induction breeding program conducted by the inventor in Fort Myers, Fla., and Salinas, Calif. The objective of the breeding program is to create new garden-type Chrysanthemum cultivars having with desirable inflorescence form and color and good garden performance.

The new cultivar originated by exposing unrooted cuttings of the Chrysanthemum cultivar Heather (disclosed in U.S. Plant Pat. No. 9,440) to X-ray radiation at a level of 1,750 rads in March, 1994. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The cultivar Soft Heather was discovered and selected by the inventor as a single flowering plant within this population in August, 1994. The selction of this plant was based on its desirable ray floret color and good form.

Asexual reproduction of the new cultivar by terminal cutting taken in a controlled environment in Salinas, Calif., has shown that the unique features of this new Chrysanthemum are stable and reproduced true to type in successive generations.

SUMMARY OF THE INVENTION

The cultivar Soft Heather has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Soft Heather'. These characteristics in combination distinguish 'Soft Heather' as a new and distinct cultivar:

1. Uniformly mounded plant habit.
2. Decorative-type inflorescences that are about 4.5 cm in diameter.
3. Attractive lavender-colored ray florets.
4. Numerous inflorescences per plant.
5. Very uniform flowering.

The new Chrysanthemum is similar to the parent cultivar Heather. However in side-by-side comparisons under commercial practice, plants of the new Chrysanthemum differed from plants of the cultivar Heather in the following characteristics:

1. Plants of the new Chrysanthemum flower about four or five days earlier than of plants of the cultivar Heather grown under natural season conditions.

2. Ray florets of plants of the new Chrysanthemum are lighter in color than ray florets of plants of the cultivar Heather.
3. Ray floret color of plants of the new Chrysanthemum fades more than ray floret color of plants of the cultivar Heather.
4. Plants of the new Chrysanthemum are more compact than plants of the cultivar Heather.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Soft Heather'.

The photograph at the bottom of the sheet comprises a close-up view of typical inflorescences of the cultivar 'Soft Heather'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar Soft Heather.

Commercial classification: Decorative-type garden chrysanthemum.

Parentage: Induced mutation of *Dendranthema grandiflora* cultivar Heather, disclosed in U.S. Plant Pat. No. 9,440.

Propagation:

*Type*.—Terminal tip cuttings.

*Time to rooting*.—Seven to ten days with soil temperatures of 21° C.

*Rooting habit*.—Fine, fibrous and well-branched.

Plant description:

*Appearance*.—Perennial herbaceous decorative-type garden Chrysanthemum. Inverted triangle. Stems initially upright, then outwardly spreading giving a uniformly mounded appearance to the plant. Freely branching with lateral branches potentially developing at every node, when pinched, about 10 laterals develop.

*Plant height*.—About 30 cm.

*Plant spread*.—About 44 cm.

*Foliage description*.—Leaf arrangement: Alternate. Length: About 4.7 cm. Width: About 4.4 cm. Apex: Mucronate. Base: Truncate. Margin: Palmately lobed, sinuses mostly parallel. Texture: Upper surface sparsely pubescent; lower surface moderately pubescent. Veins prominent on lower surface. Petiole length: About 1.1 cm. Petiole diameter: About 3 mm. Color: Young foliage upper surface: 147A. Young foliage lower surface: 147B. Mature foliage upper surface: 147A. Mature foliage lower surface: 147B. Venation upper surface: 147A to 147B. Venation lower surfaces: 147B.

Inflorescence description:

*Appearance*.—Decorative-type inflorescence form with oblong-shaped ray florets. Inflorescences borne on terminals above foliage, arising from leaf axils. Disk and ray florets arranged acropetally on a capitulum. One inflorescence per terminal with numerous inflorescences per plant, about 9 per latual stem.

*Flowering response*.—Under natural season conditions, plants flower in early October in the Northern Hemisphere, about 73 days after planting, and flower for at least three weeks depending on weather conditions.

*Inflorescence bud* (*before showing color*).—Height: About 5 mm. Diameter: About 7 mm. Phyllary color: Close to 141A.

*Inflorescence size*.—Diameter: About 4.5 cm. Depth (height): About 1.7 cm. Diameter of disc: About 2.5 mm.

*Ray florets*.—Shape: Oblong, concave; fused at base. Length: About 2.1 cm. Width: About 6 mm. Apex: Dentate. Margin: Entire. Texture: Smooth, glabrous. Orientation: Initially upright, then horizontal. Number of ray florets per inflorescence: Typically more than 150. Color: When opening, upper and lower surfaces initially close to white, then: 77A; white at base. Opened inflorescence: Upper surface: 77A to 77B to 77C. Lower surface: 77C to 77D to lighter lavender, close to 75C to 75D.

*Disc florets*.—Shape: Tubular, apex dentate. Length: About 3 mm. Width: Apex: About 1 mm. Base: About 1 mm. Number of disc florets per inflorescence: Typically about 15. Color: Immature: 154A. Mature: Apex: 9A. Mid-section and base: Whitish green.

*Peduncle*.—Aspect: Flexible, angled about 45° to the stem. Length: First peduncle: About 6.2 cm. Fourth peduncle: About 7.8 cm. Diameter: About 2 mm. Texture: Pubescent. Color: 141A.

*Reproductive organs*.—Androecium: Present on disc florets only. Anther color: 9A. Pollen: Scarce. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Soft Heather', as illustrated and described.

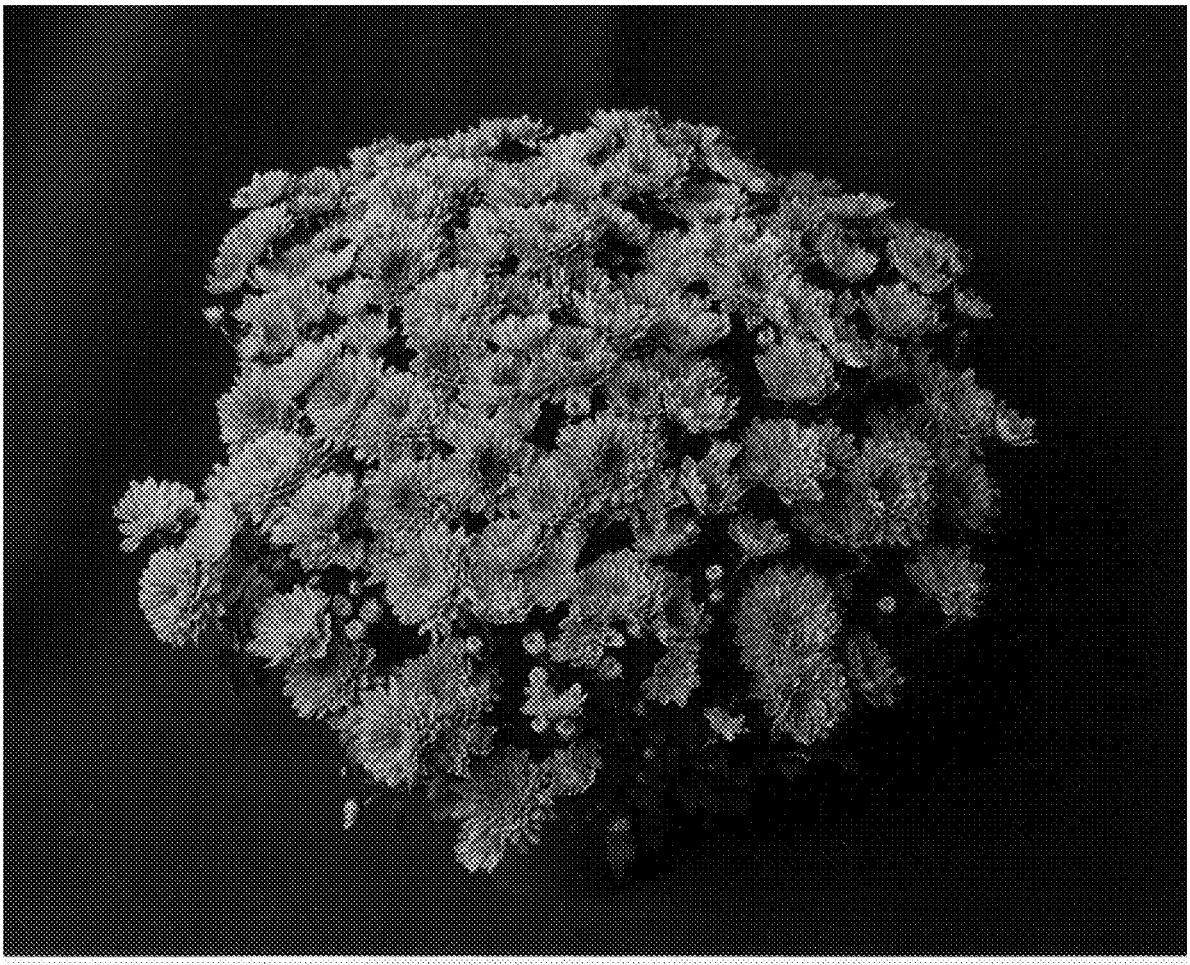
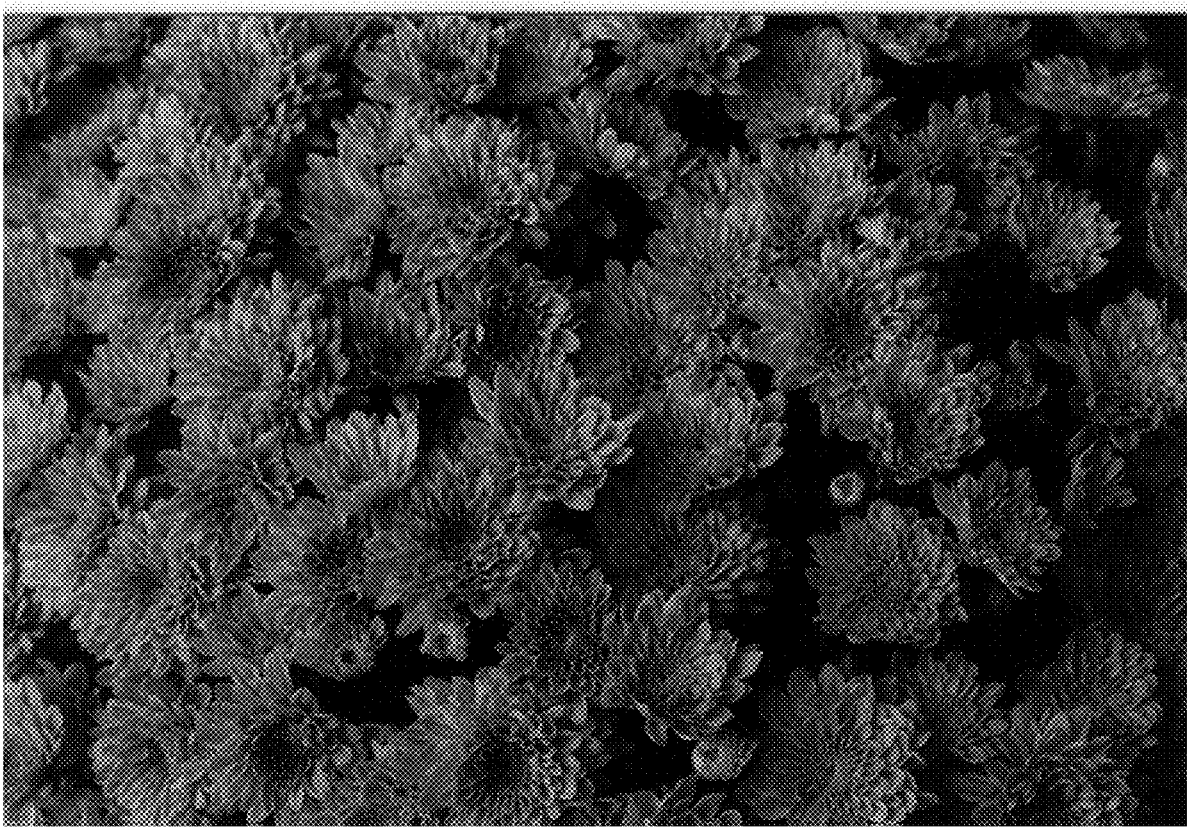

* * * * *